(12) United States Patent
Benedek et al.

(10) Patent No.: US 11,123,778 B2
(45) Date of Patent: *Sep. 21, 2021

(54) SOLID WASTE PROCESSING WITH PYROLYSIS OF CELLULOSIC WASTE

(71) Applicant: ANAERGIA INC., Burlington (CA)

(72) Inventors: Andrew Benedek, Rancho Santa Fe, CA (US); Juan Carlos Josse, Aliso Viejo, CA (US)

(73) Assignee: ANAERGIA INC., Burlington (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/083,000

(22) PCT Filed: Mar. 14, 2017

(86) PCT No.: PCT/CA2017/050336
§ 371 (c)(1),
(2) Date: Sep. 7, 2018

(87) PCT Pub. No.: WO2017/156629
PCT Pub. Date: Sep. 21, 2017

(65) Prior Publication Data
US 2019/0091739 A1 Mar. 28, 2019

Related U.S. Application Data

(60) Provisional application No. 62/310,341, filed on Mar. 18, 2016.

(51) Int. Cl.
*B09B 3/00* (2006.01)
*C10L 3/08* (2006.01)
(Continued)

(52) U.S. Cl.
CPC ............... *B09B 3/00* (2013.01); *B07C 5/342* (2013.01); *B09B 3/0083* (2013.01); *C10B 53/07* (2013.01);
(Continued)

(58) Field of Classification Search
None
See application file for complete search history.

(56) References Cited

U.S. PATENT DOCUMENTS 4,153,514 A    5/1979   Garrett et al.
4,289,625 A    9/1981   Tarman et al.
(Continued)

FOREIGN PATENT DOCUMENTS

BR    9401102 A    11/1994
CA    2628323 A1    6/2007
(Continued)

OTHER PUBLICATIONS

Huang, J., et al., Intelligent Solid Waste Processing Using Optical Sensor Based Sorting Technology, IEEE, Nov. 2010, 2010 3d International Congress on Image and Signal Processing, pp. 1657-1661. (Year: 2010).*

(Continued)

*Primary Examiner* — Derek N Mueller
(74) *Attorney, Agent, or Firm* — Borden Ladner Gervais; Michael Damiani

(57) ABSTRACT

Waste, such as municipal solid waste (MSF), is separated into a wet fraction and refuse derived fuel (RDF). For example, the waste may be separated in a press. The wet fraction is treated in an anaerobic digester. The RDF is further separated into a cellulosic fraction and a non-cellulosic fraction. The cellulosic fraction is treated by pyrolysis and produces a pyrolysis liquid. The pyrolysis liquid is added to the anaerobic digester.

9 Claims, 1 Drawing Sheet

(51) Int. Cl.

| | | |
|---|---|---|
| *C12P 5/02* | (2006.01) | |
| *C10L 5/44* | (2006.01) | |
| *F23G 5/027* | (2006.01) | |
| *C10L 9/08* | (2006.01) | |
| *C10L 5/46* | (2006.01) | |
| *B07C 5/342* | (2006.01) | |
| *C10B 53/07* | (2006.01) | |
| *C10B 57/14* | (2006.01) | |
| *C12M 1/00* | (2006.01) | |
| *B03B 9/06* | (2006.01) | |
| *B07C 5/36* | (2006.01) | |

(52) U.S. Cl.
CPC .............. *C10B 57/14* (2013.01); *C10L 3/08* (2013.01); *C10L 5/44* (2013.01); *C10L 5/46* (2013.01); *C10L 9/08* (2013.01); *C12M 43/00* (2013.01); *C12P 5/023* (2013.01); *F23G 5/027* (2013.01); *B03B 9/06* (2013.01); *B07C 5/363* (2013.01); *C10L 2290/02* (2013.01); *C10L 2290/10* (2013.01); *C10L 2290/26* (2013.01); *C10L 2290/30* (2013.01); *C10L 2290/546* (2013.01)

(56) References Cited

U.S. PATENT DOCUMENTS

| | | | |
|---|---|---|---|
| 4,522,151 | A | 6/1985 | Arbisi et al. |
| 4,759,300 | A | 7/1988 | Hansen et al. |
| 4,880,473 | A | 11/1989 | Scott et al. |
| 4,935,038 | A | 6/1990 | Wolf |
| 5,017,196 | A | 5/1991 | Dewitz |
| 5,395,455 | A | 3/1995 | Scott et al. |
| 5,417,492 | A | 5/1995 | Christian et al. |
| 5,424,417 | A | 6/1995 | Torget et al. |
| 5,605,551 | A | 2/1997 | Scott et al. |
| 5,865,898 | A | 2/1999 | Holtzapple et al. |
| 5,959,167 | A | 9/1999 | Shabtai et al. |
| 6,022,419 | A | 2/2000 | Torget et al. |
| 6,048,374 | A | 4/2000 | Green |
| 6,228,177 | B1 | 5/2001 | Torget |
| 7,229,483 | B2 | 6/2007 | Lewis |
| 7,494,637 | B2 | 2/2009 | Peters et al. |
| 7,578,927 | B2 | 8/2009 | Marker et al. |
| 7,608,439 | B2 | 10/2009 | Offerman et al. |
| 7,972,824 | B2 | 7/2011 | Simpson et al. |
| 8,119,076 | B2 | 2/2012 | Keusenkothen et al. |
| 8,383,871 | B1 | 2/2013 | Sellars et al. |
| 8,632,024 | B2 | 1/2014 | Gitschel et al. |
| 8,777,468 | B2 | 7/2014 | Suehiro et al. |
| 8,877,468 | B2 * | 11/2014 | Lewis .............. C10B 53/02 435/165 |
| 8,993,288 | B2 | 3/2015 | Lewis |
| 9,534,174 | B2 | 1/2017 | Mazanec et al. |
| 2003/0071372 | A1 | 4/2003 | Scherzinger et al. |
| 2004/0084366 | A1 | 5/2004 | Anderson et al. |
| 2006/0112639 | A1 | 6/2006 | Nick et al. |
| 2006/0289356 | A1 | 12/2006 | Burnett et al. |
| 2007/0117195 | A1 | 5/2007 | Warner et al. |
| 2007/0217995 | A1 | 9/2007 | Matsumura et al. |
| 2008/0035561 | A1 | 2/2008 | Gray |
| 2008/0236042 | A1 | 10/2008 | Summerlin |
| 2008/0280338 | A1 | 11/2008 | Hall et al. |
| 2008/0317657 | A1 | 12/2008 | Hall et al. |
| 2009/0151253 | A1 | 6/2009 | Manzer et al. |
| 2009/0229595 | A1 | 9/2009 | Schwartz, Jr. |
| 2009/0239279 | A1 | 9/2009 | Hall et al. |
| 2010/0021979 | A1 | 1/2010 | Facey et al. |
| 2010/0133085 | A1 | 6/2010 | Hutchins et al. |
| 2010/0162627 | A1 | 7/2010 | Clomburg, Jr. et al. |
| 2010/0223839 | A1 | 9/2010 | Garcia-Perez et al. |
| 2010/0317070 | A1 | 12/2010 | Agaskar |
| 2011/0033908 | A1 | 2/2011 | Cheong et al. |
| 2011/0179700 | A1 | 7/2011 | Monroe et al. |
| 2011/0248218 | A1 | 10/2011 | Sutradhar et al. |
| 2011/0278149 | A1 | 11/2011 | Hornung et al. |
| 2012/0322130 | A1 | 12/2012 | Garcia-Perez et al. |
| 2013/0134089 | A1 | 5/2013 | Cote |
| 2013/0203144 | A1 | 8/2013 | Josse et al. |
| 2013/0316428 | A1 * | 11/2013 | Gonella ............... C12P 1/04 435/170 |
| 2014/0183022 | A1 | 7/2014 | Daugaard et al. |
| 2016/0024390 | A1 | 1/2016 | Ullom |
| 2017/0240814 | A1 | 8/2017 | Dalluge et al. |

FOREIGN PATENT DOCUMENTS

| | | |
|---|---|---|
| CA | 2641270 A1 | 12/2009 |
| CN | 104609698 A | 5/2015 |
| DE | 10107712 A1 | 9/2002 |
| EP | 0359250 A2 | 3/1990 |
| EP | 0521685 A2 | 1/1993 |
| EP | 1207040 A2 | 5/2002 |
| EP | 1568478 A1 | 8/2005 |
| GB | 1571886 A | 7/1980 |
| GB | 2257137 A | 1/1993 |
| GB | 2332196 A | 6/1999 |
| JP | 2003089793 A | 3/2003 |
| WO | 0179123 A1 | 10/2001 |
| WO | 2004060587 A1 | 7/2004 |
| WO | 2006056620 A1 | 6/2006 |
| WO | 2010001137 A2 | 1/2010 |
| WO | 2011128513 A1 | 10/2011 |
| WO | 2012166771 A2 | 12/2012 |
| WO | 2013110186 A1 | 8/2013 |
| WO | 2015050433 A1 | 4/2015 |
| WO | 2015053617 A1 | 4/2015 |
| WO | 2017161445 A1 | 9/2017 |

OTHER PUBLICATIONS

ASTM, Section D3172, Proximate Analysis of Coal and Coke, (2007), 2 pages.
AWWTA, Standard Methods, Section 2540G, (2000).
Bredwell et al., "Reactor Design Issues for Synthesis-Gas Fermentations, Biotechnology Process," Biotechnology Process, 1999, vol. 15 (5), pp. 834-844.
Bridgewater., et al., "An Overview of Fast Pyrolysis of Biomass", Organic Geochemistry, Dec. 1999, vol. 30 (12), pp. 1479-1493. Retrieved from the Internet:[https://www.researchgate.net/profile/Dietrich_Meier/publication/222485410_An_Overview_of_Fast_pyrolysis_of_Biomass/links/02bfe512926de56965000000.pdf].
Canadian Patent Application No. 2,862,132, Office Action dated Mar. 5, 2019.
Chen et al., "Pyrolysis Technologies for Municipal Solid Waste: A Review," Waste management, Dec. 2014, vol. 34 (12), pp. 2466-2486.
Corporate Literature., "Pacific Pyrolysis—Technology", Pacific Pyrolysis Corp., Jun. 2017, 4 pages. Retrieved from the Internet: [http://pacificpyrolysis.com/technology.html].
Cozzani et al., "A Fundamental Study on Conventional Pyrolysis of a Refuse-Derived Fuel," Industrial & Engineering Chemistry Research, Jun. 1995, 34, pp. 2006-2020.
Demirbas et al., "Biomass Resource Facilities and Biomass Conversion Processing for Fuels and Chemicals," Energy Conversion and Management, Jul. 2001, vol. 42 (11), pp. 1357-1378.
Demirbas et al., "The Influence of Temperature on the Yields of Compounds Existing in Bio-Oils Obtained from Biomass Samples via Pyrolysis," Fuel Processing Technology, Jun. 2007, vol. 88 (6), pp. 591-597.
European Patent Application No. 13740592.4, Office Action dated Aug. 23, 2018.
European Patent Application No. 17765614.7, Extended European Search Report dated Nov. 8, 2019.
European Patent Application No. 17769208.4, Extended European Search Report dated Oct. 18, 2019.
European Patent Application No. 13740592, Supplementary European Search Report dated Jul. 27, 2015.

(56) References Cited

OTHER PUBLICATIONS

European Patent Application No. 13740592.4, Communication pursuant to Article 94(3) EPC dated Jan. 17, 2018.
European Patent Application No. 16162806, Extended European Search Report dated Dec. 14, 2016.
Fabbri et al., "Linking Pyrolysis and Anaerobic Digestion (Py-AD) for the Conversion of Lignocellulosic Biomass," Current Opinion in Biotechnology, Apr. 2016, vol. 38, pp. 167-173. XP029496680.
Garcia-Perez, "Challenges and Opportunities of Biomass Pyrolysis to Produce Second Generation Bio-fuels and Chemicals," Auburn University, Jun. 13, 2012, 66 pages.
Georges Bruhat, Excerpts from Traite De Polarimetrie, Paris, France, 1930, 2 pages.
Gomes et al., "Methodology for Burner Design-Combustion of Pyrolysis Gas from Charcoal Production," 24th ABCM International Congress of Mechanical Engineering, Dec. 3-8, 2017, 7 pages.
Guiot et al., "Potential of Wastewater-Treating Anaerobic Granules for Biomethanation of Synthesis Gas," Environmental Science and Technology, Feb. 2011, vol. 45 (5), pp. 2006-2012.
Gullu et al., "Biomass to Methanol via Pyrolysis Process," Energy Conversion and Management, Jul. 2001, vol. 42 (11), pp. 1349-1356.
International Patent Application No. PCT/CA2013/050037, International Preliminary Report on Patentability dated Aug. 7, 2014.
International Patent Application No. PCT/CA2013/050037, International Search Report dated Apr. 4, 2013.
International Patent Application No. PCT/CA2014/050662, International Preliminary Report on Patentability dated Jan. 21, 2016.
International Patent Application No. PCT/CA2014/050662, International Search Report and Written Opinion dated Sep. 25, 2014.
International Patent Application No. PCT/CA2016/050103, International Search Report and Written Opinion dated May 26, 2016.
International Patent Application No. PCT/CA2017/050335, International Search Report and Written Opinion dated Jun. 22, 2017.
International Patent Application No. PCT/CA2017/050336, International Search Report and Written Opinion dated Jun. 22, 2017.
International Patent Application No. PCT/CA2019/051240, International Search Report and Written Opinion dated Nov. 14, 2019.
Jenkins, "Oxidation-Based Water-Reuse Technology that Improves Mass Transfer," Chemical Engineering, Feb. 2013, p. 12.
Jones, et al., "Production of Gasoline and Diesel from biomass via Fast Pyrolysis" Hydrotreating and Hydrocracking: A Design Case, U.S. Department of Energy, PNNL-18284 Feb. 28, 2009, 76 pages.
Laemsak, "Wood Vinegar Presentation," Undated, 5 pages.
Laird et al., "Sustainable Alternative Fuel Feedstock Opportunities, Challenges and Roadmaps for Six U.S. Regions," Chapter 16: Pyrolysis and Biochar—Opportunities for Distributed Production and Soil Quality Enhancement, Proceedings of the Sustainable Feedstocks for Advance Biofuels Workshop, Atlanta, GA, Sep. 28-30, 2010, pp. 257-281.
Lehmann et al., "Bio-Char Sequestration in Terrestrial Ecosystems—A Review ," Mitigation and Adaptation Strategies for Global Change , Mar. 2006, vol. 11 (2), pp. 403-427.
Lewis et al., "A Powerful by Product," WEFTEC, Jan. 2008, pp. 64-69.
Lian et al., "Separation, Hydrolysis and Fermentation of Pyrolytic Sugars to Produce Ethanol and Lipids," Bioresource Technology, Dec. 2010, vol. 101 (24), pp. 9688-9699.
Liaw et al., "Effect of Pyrolysis Temperature on the Yield and Properties of Bio-oils Obtained From the Auger Pyrolysis of Douglas Fir Wood," Journal of Analytical and Applied Pyrolysis, Jan. 2012, vol. 93, pp. 52-62.
Linden et al., "Gaseous Product Distribution in Hydrocarbon Pyrolysis," Industrial and Engineering Chemistry, 1955, vol. 47 (12), pp. 2470-2474.
Mahulkar et al., "Steam Bubble Cativation," AIChE Journal, Jul. 2008, vol. 54 (7), pp. 1711-1724.
Mckendry., "Energy Production from Biomass (Part 3): Gasification Technologies," Bioresource Technology, May 2002, vol. 83 (1), pp. 55-63. Retrieved from the Internet: [https://eclass.duth.gr/modules/document/file.php/].
Melin et al., "Evaluation of Lignocellulosic Biomass Upgrading Routes to Fuels and Chemicals," Cellulose Chemistry and Technology, 2010, vol. 44 (4-6), pp. 117-137.
Parry, Biosolids Technology Advances, Jan. 2012, 20 Pages.
Parry, et al. "Prolysis of Dried Biosolids for Increased Biogas Production" Proceedings of the Water Environment Federation, Residuals and Biosolids, Mar. 2012, pp. 1128-1139.
Shanley Pump and Equipment, Inc., EDUR Pumps, [online], printed May 30, 2014. Retrieved from the Internet: http://www.shanleypump.com/edur_pumps.html.
Smith et al., "Integrating Pyrolysis and Anaerobic Digestion," The Northwest Bio-energy Symposium, Seattle, Washington, Nov. 13, 2012, 44 pages, http://www.pacificbiomass.org/documents/Smith.pdf.
Sustarsic, "Wastewater Treatment: Understanding the Activated Sludge Process" CEP Nov. 2009, pp. 26-29.
U.S. Appl. No. 14/903,904, Final Office Action dated Dec. 14, 2018.
U.S. Appl. No. 15/389,901, Restriction Requirement dated Feb. 26, 2019.
U.S. Appl. No. 16/124,763, Non-Final Office Action dated Sep. 25, 2019.
U.S. Appl. No. 14/903,904, Non-Final Office Action dated Apr. 19, 2018.
U.S. Appl. No. 13/136,180, Notice of Allowance dated Jul. 8, 2014.
U.S. Appl. No. 13/136,180, Notice of Allowance dated Mar. 4, 2014.
U.S. Appl. No. 13/136,180, Office Action dated Mar. 20, 2013.
U.S. Appl. No. 13/136,180, Office Action dated Nov. 2, 2012.
U.S. Appl. No. 13/826,507, Advisory Action dated May 22, 2015.
U.S. Appl. No. 13/826,507, Notice of Allowance dated Sep. 29, 2016.
U.S. Appl. No. 13/826,507, Office Action dated Feb. 26, 2016.
U.S. Appl. No. 13/826,507, Office Action dated Jul. 7, 2014.
U.S. Appl. No. 13/826,507, Office Action dated Mar. 18, 2015.
U.S. Appl. No. 13/826,507, Restriction Requirement dated Apr. 11, 2014.
U.S. Appl. No. 14/031,758, Notice of Allowance dated Nov. 28, 2014.
U.S. Appl. No. 14/031,758, Office Action dated Apr. 28, 2014.
U.S. Appl. No. 14/373,714, Notice of Allowance dated Nov. 10, 2015.
U.S. Appl. No. 14/373,714, Office Action dated Jul. 24, 2015.
U.S. Appl. No. 14/631,144, Notice of Allowance dated Apr. 15, 2016.
U.S. Appl. No. 14/631,144, Office Action dated Nov. 12, 2015.
U.S. Appl. No. 14/903,904, Advisory Action dated Dec. 6, 2017.
U.S. Appl. No. 14/903,904, Final Office Action dated Jul. 31, 2017.
U.S. Appl. No. 14/903,904, Office Action dated Jan. 17, 2017.
U.S. Appl. No. 15/015,479, Notice of Allowance dated Sep. 8, 2017.
U.S. Appl. No. 15/015,479, Office Action dated Feb. 24, 2017.
U.S. Appl. No. 15/085,381, Notice of Allowance dated Sep. 21, 2017.
U.S. Appl. No. 15/085,381, Office Action dated Apr. 19, 2017.
U.S. Appl. No. 15/389,901, Non-Final Office Action dated Jul. 22, 2019.
U.S. Appl. No. 16/124,763, Final Office Action dated Jan. 17, 2020.
Water and Sewage Treatment Energy Management Joint Conference, Delaware Valley Regional Planning Commission, Apr. 25, 2012, 55 Pages.
Woolf et al., "An Open-Source Biomass Pyrolysis Reactor," Biofuels, Bioproducts, and Biorefining, Sep. 2017, vol. 11 (6), pp. 945-954.
Written Opinion for Application No. PCT/CA2013/050037, dated Apr. 4, 2013, 7 pages.
Yang et al., "Pretreatment: The Key to Unlocking Low-Cost Cellulosic Ethanol," Biofuels, Bioproducts and Eliorefinering, Jan. 2008, vol. 2 (1), pp. 26-40.
Zanzi et al., "Rapid Pyrolysis of Agricultural Residues at High Temperature," Biomass and Bioenergy, Nov. 2002, vol. 23 (5), 4 pages.

(56) References Cited

OTHER PUBLICATIONS

Zhang et al., "Influence of Manure Types and Pyrolysis Conditions on the Oxidation Behavior of Manure Char," Bioresource Technology, Sep. 2009, vol. 100 (18), pp. 4278-4283.
International Patent Application No. PCT/CA2017/050336, International Preliminary Report on Patentability dated Sep. 18, 2018.
U.S. Appl. No. 14/903,904, Non-Final Office Action dated Dec. 31, 2019.
U.S. Appl. No. 16/124,763, Non-Final Office Action dated May 4, 2020.
U.S. Appl. No. 15/705,704, Restriction Requirement dated Feb. 28, 2020.
U.S. Appl. No. 16/124,763, Final Office Action dated Sep. 14, 2020.
Chinese Patent Application No. 201610542016.4, Office Action dated Jun. 23, 2020—English Translation Available.
Chinese Patent Application No. 201610542016.4, Office Action dated Jan. 13, 2021—English Translation Not Available.
International Patent Application No. PCT/CA2016/050103, International Preliminary Report on Patentability dated Aug. 17, 2017.
International Application No. PCT/CA2017/050335, International Preliminary Report on Patentability dated Oct. 4, 2018.
International Application No. PCT/CA2017/050336, International Preliminary Report on Patentability dated Sep. 27, 2018.
International Application No. PCT/CA2019/051240, International Preliminary Report on Patentability dated Mar. 18, 2021.
U.S. Appl. No. 14/903,904, Final Office Action dated Nov. 23, 2020.
U.S. Appl. No. 16/124,763, Non-Final Office Action dated Feb. 11, 2021.
U.S. Appl. No. 14/903,904, Non-Final Office Action dated Mar. 4, 2021.
Singapore Patent Application No. SG10201908192U, Written Opinion dated Sep. 17, 2020.
U.S. Appl. No. 16/124,763, Advisory Action dated Nov. 23, 2020.

\* cited by examiner

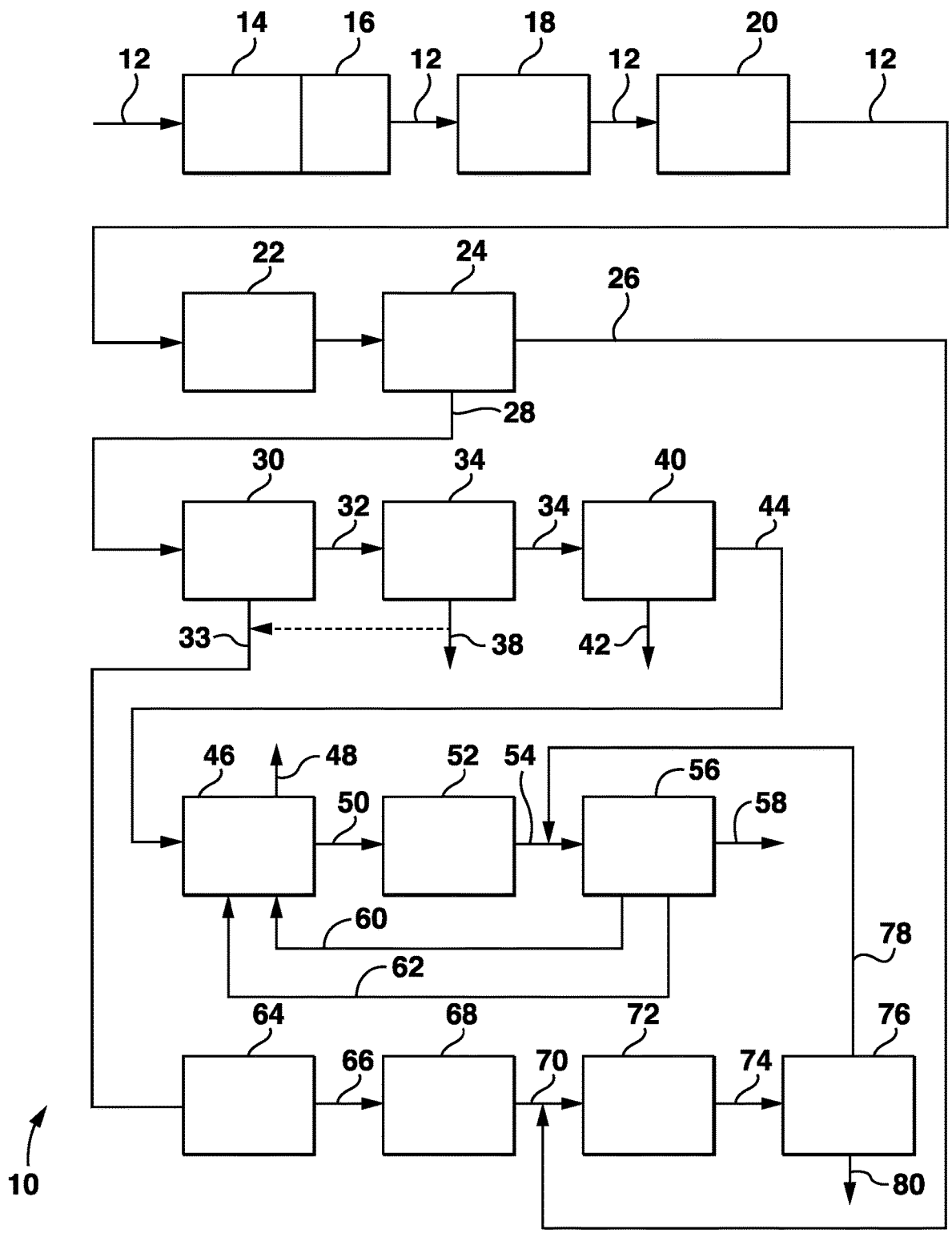

SOLID WASTE PROCESSING WITH PYROLYSIS OF CELLULOSIC WASTE

CROSS-REFERENCE TO RELATED APPLICATIONS

This application is a National Stage Entry of International Application No. PCT/CA2017/050336, filed Mar. 14, 2017, which is a non-provisional application of U.S. Application Ser. No. 62/310,341, filed Mar. 18, 2016. International Application No. PCT/CA2017/050336 and U.S. Application Ser. No. 62/310,341 are incorporated by reference.

FIELD

This specification relates to treating waste such as municipal solid waste (MSW).

BACKGROUND

US Publication 2013/0316428 describes a process in which an organic fraction containing biological cells is separated from solid urban waste. The organic fraction is extruded through a grid having small-bore holes, under a pressure higher than the burst pressure of the cell membranes. The cells are disrupted and a gel of a doughy consistency is produced. The gel is then loaded into a biodigester, where it is readily attacked by bacteria. The press may be as described in European Publication Nos. 1207040 and 1568478. In general, these presses use a plunger to compress waste that has been loaded into a cylinder. The sides of the cylinder are perforated with radial holes. US Publication 2013/0316428 and European Publication Nos. 1207040 and 1568478 are incorporated herein by reference.

U.S. Pat. No. 8,877,468 describes a process in which materials containing lignocellulose are treated by pyrolysis under conditions (low temperature and long residence time) that favour the production of a liquid containing organic acids and alcohols. This liquid is suitable for conversion to biogas (primarily methane) in an anaerobic digester. U.S. Pat. No. 8,877,468 is incorporated herein by reference.

INTRODUCTION

Waste, such as municipal solid waste, is separated into a wet fraction and refuse derived fuel (RDF). For example, the waste may be separated in a press, or by a screen followed by a press. The wet fraction is treated in an anaerobic digester. The RDF is further separated into a cellulosic fraction and a non-cellulosic fraction. The cellulosic fraction is treated by pyrolysis and produces a pyrolysis liquid. The pyrolysis liquid is added to the anaerobic digester. Digestate from the anaerobic digester may be treated by pyrolysis.

BRIEF DESCRIPTION OF THE FIGURES

FIG. 1 is a schematic drawing of a solid waste treatment system.

DETAILED DESCRIPTION

FIG. 1 shows a system 10 for treating solid waste 12. Solid waste 12, which may be for example municipal solid waste (MSW), is collected in trucks and dumped in piles in a tipping floor or pit 14. A loader or grapple places the waste into a dosing feeder 16 that feeds waste 12 into the processing line conveyor at a generally consistent rate suitable for the downstream processes. The waste 12 travels on the conveyor through a pre-sorting area 18. In the pre-sorting area 18, large un-bagged bulky items and other non-processible materials (such as furniture, rolls of chainlink fence, carpets, toilet bowls, etc are manually removed from the conveyor.

The waste 12 continues from the pre-sorting area 18 and drops into a bag opener 20. The bag opener 20 opens plastic garbage bags. For example, the bag opener 20 may use a coarse tearing shredder, for example a single or double shaft shredder with a 200 mm spacing, to open the bags. The waste 12 with opened bags is then placed on another conveyor.

The waste 12 continues on the conveyor below an overbelt magnet 22 to remove large ferrous metal items. The waste 12 then passes through a coarse screen 24. The coarse screen 24 may be, for example, a disc or roller screen with 100-150 mm openings. The coarse screen 24 retains some of the waste 12, for example about 30-40%, as coarse screen overs 26. The screen overs 26 contain mostly large, generally dry, items of waste. The remaining 60-70% of the waste 12 passes through the coarse screen 24 and becomes coarse screen unders 28. The coarse screen unders 28 contain mostly wet or organic matter such as food waste, small containers and some inerts. In an efficient coarse screening process, about 95% of food waste in the waste 12 may end up in the coarse screen unders 28.

The coarse screen unders 28 are treated in a press 30. The press 30 compresses the coarse screen unders 28 at high pressure through small perforations in an enclosed extrusion chamber. For example, the pressure may be at least 50 bar or otherwise sufficient to mobilize the putrescible organic material through the perforations. The organics are separated from the rest based on their viscosity. The perforations may be, for example, 4 to 20 mm diameter circular holes. The press 30 separates the coarse screen unders 28 into a wet fraction 32, which passes through the perforations, and rejects 33 that remain in the extrusion chamber after compression. The wet fraction 32 contains soluble organic compounds and particulate material. Roughly half of the coarse screen unders 28 is retained as rejects 33. Preferably, 95% or more of the organics in the coarse screen unders 28 is contained in the wet fraction 32.

The press 30 may be as described in International Publication Number WO 2015/053617, Device and Method for Pressing Organic Material Out of Waste, or as described in European Publication Nos. 1207040 and 1568478, all of which are incorporated herein by reference. Suitable presses are sold by DB Italy and DB Technologies. Other presses may also be used.

Other means of separating the coarse screen unders 28 may also be used. For example, the coarse screen unders 28 can be milled under high force shearing, hammering, or pulverizing in order to dislodge material and separate a wet fraction 32 containing organics from a dry fraction equivalent to rejects 33. For example, a hammer mill can violently dislodge organics and break large organic pieces into small particles or produce a slurry. In some cases, the mill may require dilution of the coarse screen unders 28. The organics can be recovered separated from the dry fraction by a screen that retains the dry fraction and permits the passage of organics driven by the hammering or other shearing force. Alternatively, the pulverized mixture of organics and dry fraction can pass through the mill and into a screw press that separates the organic slurry and water from the dry fraction through a screen.

The wet fraction 32 passes into a polisher 34. In the polisher 34, the wet fraction 32 is fed into a screen cylinder surrounding a rotor. Particles of organic matter in the wet fraction 32 are flung outward from a rotor by its rotating movement and centrifugal forces. The particles of organic material are discharged through perforations in the screen to a first discharge opening. Air flowing along the axis of the rotor carries lighter material past the perforations to a second discharge opening. The airflow may be created by the rotor blades or by a separate fan. The rotor blades may optionally also scrape the inside of the screen. In this way, lighter particles (particularly bits of plastic) are separated from the organic particles in the wet fraction 32. The polisher 34 thereby produces polished wet fraction 36 and floatables 38. The floatables 38 include small pieces of plastic and paper that would tend to collect at the top of an anaerobic digester. A suitable polisher 34 is described in International Publication Number WO 2015/050433, which is incorporated herein by reference. A similar polisher is sold as the DYNAMIC CYCLONE by DB Technologies. Floatables 38 can be sent to landfill or optionally combined with rejects 33.

The polished wet fraction 36 is treated in a grit removal unit 40. The grit removal unit 40 preferably includes a hydro-cyclone. Water may be added if required to dilute the polished wet fraction 36 to bring its solids content to or below the maximum solids content accepted by the grit removal unit 40. The grit removal unit 40 removes grit 42 large enough to settle in an anaerobic digester. Separated grit 42 is sent to landfill, optionally after rinsing it. One suitable grit removal unit is the PRO:DEC system by CD Enviro.

Degritted wet fraction 44 is sent to an anaerobic digester 46, alternatively referred to as a digester for brevity. The digester 46 may have one or more mixed covered tanks. Suitable digesters are sold under the Triton and Helios trade marks by UTS Biogas or Anaergia. The digester 46 produces product biogas 48 which may, for example, be used to produce energy in a combined heat and power unit or upgraded to produce biomethane. The digester 46 also produces sludge 50.

Sludge 50, alternatively called digestate, is sent to a drying unit 52. In the drying unit 52, the sludge is treated in a mechanical dewatering unit, for example a centrifuge, filter press or screw press. The mechanical dewatering unit separates the sludge 50 into a waste liquid, which may be sent to a sanitary drain or treated on site for discharge or re-use, and a de-watered cake. The de-watered cake is sent to a sludge cake dryer to further reduce its water content. Preferably, the de-watered cake is formed into pellets 54. The pellets 54 may be transported, for example, by screw conveyors or in bags or bins.

Pellets 54 are sent to a pyrolysis reactor 56. The pyrolysis reactor 56 heats the pellets 54 in the absence or a deficiency of oxygen, to produce biochar 58, pyrolysis liquid 60 and pyrolysis gas 62.

The biochar 58 may be sold as a soil enhancer, sent to landfill or processed further, for example in a gasification plant to make syngas. Pyrolysis liquid 60, including condensed vapors, is recycled to anaerobic digester 46 as additional feedstock for digestion. Pyrolysis gas 62 is also sent back to the digester 46. The pyrolysis gas 62 may be injected into the bottom of the digester 46. The pyrolysis gas 62 is scrubbed to some extent as it rises in bubbles though sludge in the digester 46, and then mixes with biogas 48 in the headspace of the digester 46. Part of the pyrolysis gas 62, particularly the hydrogen, may also be transferred into the sludge and be biologically converted to methane. The transfer of pyrolysis gas 62 to sludge in the digester 46 can optionally be enhanced by injecting the pyrolysis gas 62 as fine bubbles, by adding the pyrolysis gas through a dissolution cone into a stream of recirculating sludge, or by recirculating the headspace gas. Optionally, if the recycle of pyrolysis gas 62 increases the concentration of carbon monoxide (CO) in the biogas 48 too much, CO can be removed from the pyrolysis gas 62 or biogas 48 by membrane separation, or the pyrolysis gas 62 can be at least partially converted to methane before being added to the digester 46.

The temperature in the pyrolysis reactor 56 may be over 270 degrees C., preferably over 300 degrees C., more preferably over 320 degrees C., but less than 450 degrees C., preferably less than 400 degrees C. and more preferably less than 350 degrees C. The residence time may be 5-30 minutes, but preferably 10-20 minutes. Pyrolysis of cellulosic material at over 450 degrees C. produces an excess of oils that may be toxic to microorganisms in an anaerobic digester. Pyrolysis at lower temperatures produces even less of the toxic substances and also produces more pyrolysis liquid 60 relative to pyrolysis gas 62. This is beneficial since the pyrolysis liquid 60 is easily mixed into sludge in the anaerobic digester 46 and enhances production of biogas 48. However, at very low temperatures the production of biochar 58 dominates and more material must be removed from the system 10. A temperature of 320 to 350 degrees and residence time of about 10-20 minutes is particularly useful.

Rejects 33 are sent to a shredder 64. The rejects 33 emerge from press 30 as chunks having about 38-50% water by weight. The chunks may have an average volume of about 0.02 to 0.1 cubic meters. The shredder 64 may have, for example, a single shaft crusher or shredder. The shredder 64 breaks up the chunks and produces shredded rejects 66.

The shredded rejects 66 are sent to a vibrating screen 68. The vibrating screen 68 may have 30 mm to 50 mm openings. Inerts and remaining organic materials fall through screen vibrating screen 68 and may be sent to landfill. Vibrating screen overs 70 includes solids such as plastic bottles, bags, fabric, and paper. Aluminum cans may also be present in the overs. If so, an eddy current separator can be used to remove non-ferrous metals. A drum magnet may also be used to remove remaining small pieces of ferrous material metal, if any.

The vibrating screen overs 70 are combined with coarse screen overs 26. Optionally, the coarse screen overs 26 may have first passed through additional recyclable recovery units. Recyclables can be recovered, for example by manual separation, optical sorters or ballistic separators.

The combined overs 26, 70 then pass through a wind sorter 72. In the wind sorter 72, air nozzles blow material from one belt to another over a gap. RDF fluff 74 flies over the gap. Dense material, i.e. rocks, falls into the gap and is sent to landfill. The RDF fluff 74 has about 25% moisture and contains plastic, paper, textiles, other dry fibers, etc.

The RDF fluff 74 goes to an optical sorter 76. The optical sorter 76 separates plastic and other non-cellulosic material from cellulosic material such as wood and paper. Near infrared sensors determine if matter is cellulosic or not. Air jets then separate the RDF fluff 74 into cellulosic fluff 78 and non-cellulosic 80 fluff with about 85-95% efficient separation.

Non-cellulosic fluff 80 is sent off-site. The non-cellulosic fluff 80 could be combusted to recover heat energy or converted to bio-oil by pyrolysis. If pyrolysis is used, this is a high temperature, low residence time process that emphasizes the production of long chain hydrocarbons. Bio-oil produced from plastics in this way is useful in making fuels but toxic to microorganisms in digester 46.

Cellulosic fluff 78 is sent to pyrolysis unit 56. The cellulosic fluff 78 is treated as described for pellets 54 and increases the production of pyrolysis liquid 60 and pyrolysis gas 62. Due to the low pyrolysis temperature described above, plastics remaining in the cellulosic fluff 78 do not break down and tend to pass through to the biochar 58. The plastics do not therefore add materials toxic to the digester 46 to the pyrolysis liquid 60 or pyrolysis gas 62.

We claim:

1. A process for treating solid waste comprising steps of, separating the waste to produce rejects and a wet fraction; separating cellulosic rejects from the rejects; and, treating at least a portion of cellulosic rejects by anaerobic digestion.

2. The process of claim 1 further comprising co-digesting the wet fraction with the at least a portion of cellulosic rejects.

3. The process of claim 1 wherein the step of separating the waste comprises pressing the waste.

4. The process of claim 1 wherein the solid waste comprises municipal solid waste.

5. The process of claim 1 wherein the step of separating rejects comprises using an optical sorter.

6. The process of claim 1 further comprising a steps of: separating the waste to produce coarse screen overs; separating cellulosic material from the coarse screen overs; and digesting a portion of the cellulosic material.

7. The process of claim 6 wherein the portion of cellulosic material comprises pyrolysis liquid.

8. The process of claim 1 wherein the portion of cellulosic rejects comprises pyrolysis liquid.

9. The process of claim 1, wherein the step of separating the waste to produce rejects and a wet fraction comprises separating the waste to produce coarse screen unders and separating the coarse screen unders to produce rejects and a wet fraction.

* * * * *